(12) United States Patent
Srinivas et al.

(10) Patent No.: US 8,057,707 B2
(45) Date of Patent: Nov. 15, 2011

(54) COMPOSITIONS TO MITIGATE COKE FORMATION IN STEAM CRACKING OF HYDROCARBONS

(75) Inventors: Vijay R. Srinivas, Exton, PA (US); Francis Humblot, Lanneplaa (FR)

(73) Assignee: Arkems Inc., King of Prussia, PA (US)

( * ) Notice: Subject to any disclaimer, the term of this patent is extended or adjusted under 35 U.S.C. 154(b) by 165 days.

(21) Appl. No.: 12/403,620

(22) Filed: Mar. 13, 2009

(65) Prior Publication Data

US 2009/0283451 A1 Nov. 19, 2009

Related U.S. Application Data

(60) Provisional application No. 61/037,012, filed on Mar. 17, 2008.

(51) Int. Cl.
*C09K 15/10* (2006.01)
*C09K 15/12* (2006.01)
*C09K 3/00* (2006.01)
*C10G 75/02* (2006.01)
*C10G 75/04* (2006.01)
*C10G 9/16* (2006.01)
*C07C 4/02* (2006.01)
*C07C 4/04* (2006.01)

(52) U.S. Cl. .............. 252/406; 252/182.29; 208/48 R; 208/48 AA; 585/648; 585/650

(58) Field of Classification Search ............ 208/48 R, 208/48 AA; 585/648, 650; 252/406, 182.29
See application file for complete search history.

(56) References Cited

U.S. PATENT DOCUMENTS

| | | | |
|---|---|---|---|
| 3,884,884 A | 5/1975 | Scoggins et al. | |
| 4,105,540 A | 8/1978 | Weinland | |
| 4,116,812 A | 9/1978 | Godar et al. | |
| 4,404,087 A | 9/1983 | Reed et al. | |
| 4,507,196 A | 3/1985 | Reed et al. | |
| 4,511,405 A | 4/1985 | Reed et al. | |
| 4,551,227 A | 11/1985 | Porter et al. | |
| 4,552,643 A | 11/1985 | Porter et al. | |
| 4,599,480 A | 7/1986 | Buddell et al. | |
| 4,613,372 A | 9/1986 | Porter et al. | |
| 4,666,583 A | 5/1987 | Porter et al. | |
| 4,686,201 A | 8/1987 | Porter et al. | |
| 4,687,567 A | 8/1987 | Porter et al. | |
| 4,692,234 A | 9/1987 | Porter et al. | |
| 4,804,487 A | 2/1989 | Reed et al. | |
| 5,015,358 A | 5/1991 | Reed et al. | |
| 5,208,069 A | 5/1993 | Clark et al. | |
| 5,413,813 A | 5/1995 | Cruse et al. | |
| 5,424,095 A | 6/1995 | Clark et al. | |
| 5,457,234 A * | 10/1995 | Shaw | 568/21 |
| 5,463,159 A * | 10/1995 | Callejas et al. | 585/648 |
| 5,565,087 A | 10/1996 | Brown et al. | |
| 5,616,236 A | 4/1997 | Brown et al. | |
| 5,733,438 A | 3/1998 | Tong et al. | |
| 5,777,188 A * | 7/1998 | Reed et al. | 585/648 |
| 5,922,192 A * | 7/1999 | Zimmermann et al. | 208/48 R |
| 5,954,943 A * | 9/1999 | Tong et al. | 208/48 R |
| 6,020,534 A * | 2/2000 | Choudhary et al. | 585/652 |
| 6,022,472 A | 2/2000 | Herrebout et al. | |
| 6,093,260 A | 7/2000 | Petrone et al. | |
| 6,673,232 B2 * | 1/2004 | Lindstrom | 208/48 R |
| 7,604,730 B1 * | 10/2009 | Humblot et al. | 208/48 R |
| 2002/0029514 A1 * | 3/2002 | Lindstrom | 44/640 |
| 2006/0046924 A1 * | 3/2006 | Lacombe et al. | 502/34 |
| 2009/0283451 A1 * | 11/2009 | Srinivas et al. | 208/48 AA |

FOREIGN PATENT DOCUMENTS

| | | | |
|---|---|---|---|
| GB | 1552284 | | 9/1979 |
| RU | 1130627 | | 12/1984 |
| WO | WO 01/21731 | * | 3/2001 |

OTHER PUBLICATIONS

Grace, K.Y., et al., Suppresion of Coke Formation in the Steam Cracking of Alkanes: Ethane and Propane, Ind. Eng. Chem. Res., 1998, 37, pp. 901-907.

* cited by examiner

*Primary Examiner* — Joseph D Anthony

(74) *Attorney, Agent, or Firm* — Steven D. Boyd

(57) ABSTRACT

The invention relates to a combination of compounds and a process using such combination useful for reducing or preventing coke formation in thermal cracking furnaces such as ethylene steam crackers. The combination is comprised of one or more compound of the formula $R-S_x-R'$ and one or more compound selected from the following group: $R_1R_2CS_3$; $R_1R_2C=CR_3R^4$; $RSH$; $R_1S_xR_2$; $R_1R_2CH_2$; $R_1R_2R_3R_4(C_4S)$; and $R_1R_2R_3R_4R_5R_6Si_2O$.

1 Claim, No Drawings

COMPOSITIONS TO MITIGATE COKE FORMATION IN STEAM CRACKING OF HYDROCARBONS

This application claims the benefit of U.S. Provisional Patent Application No. 61/037,012, filed Mar. 17, 2008.

FIELD OF THE INVENTION

The present invention relates to compositions or combinations of compounds that mitigate coke formation in thermal cracking furnaces.

BACKGROUND OF THE INVENTION

In the production of olefins, ethylene in particular, a typical hydrocarbon stream like ethane, propane, butane, naphtha and gas oil, is pyrolyzed at high temperatures in a thermal furnace. The product is a mixture of olefins which are separated downstream. In the production of ethylene, typically water is co-injected with the hydrocarbon feed to act as a heat transfer medium and as a promoter of coke gasification. Typically, a minor but technologically important byproduct of hydrocarbon steam cracking is coke. Steam from the water co-injected reacts with the coke to convert it partially to carbon monoxide and hydrogen. Because of the accumulative nature, coke deposits build up on the reactor walls thus increasing both the tube temperatures and the pressure drop across the tube. This requires shutting down the process for decoking. This periodic shutdown results in an estimated $2 billion in lost ethylene production per year. In addition there is a direct relationship between the amount of coking and the yield of the olefin, indicating that the coke is formed at the expense of product olefin.

It is common practice in commercial ethylene production to co-inject along with the hydrocarbons, small amounts of sulfur containing compounds such as hydrogen sulfide ($H_2S$), dimethyl sulfide (DMS) or dimethyl disulfide (DMDS) to minimize coke formation. It has been proposed that the sulfur passivates the active metal surface known to be a catalyst for coke formation. In addition, the sulfur compounds are known to reduce the formation of carbon monoxide (CO), formed by the reaction of hydrocarbons or coke with steam, again by passivating the catalytic action of the metal surface and by catalyzing the water gas shift reaction which converts the CO to carbon dioxide ($CO_2$). Minimizing the amount of CO formed is essential for the proper functioning of downstream reduction operations.

U.S. Pat. No. 4,404,087 discloses that pretreating cracking tubes with compositions containing tin (Sn) compounds, antimony (Sb) and germanium (Ge) reduces the rate of coke formation, during the thermal cracking of hydrocarbons.

Combinations of Sn, Sb and Si are disclosed to do the same in U.S. Pat. No. 4,692,234.

Mixtures of chromium and antimony compounds, chromium and tin compositions, and antimony and chromium compositions have also been claimed to reduce coke formation, as measured by a time weighted CO selectivity index (U.S. Pat. No. 4,507,196).

Several phosphorous and sulfur compound combinations are disclosed (U.S. Pat. No. 5,954,943) with Sn and Sb compounds (U.S. Pats. Nos. 4,551,227; 5,565,087 and 5,616, 236), for decreasing the coke formed in hydrocarbon pyrolysis furnaces.

In general, U.S. Pats. Nos. 4,507,196; 4,511,405; 4,552, 643; 4,613,372; 4,666,583; 4,686,201; 4,687,567; 4,804,487; and 5,015,358, teach that the metals Sn, Ti, Sb, Ga, Ge, Si, In, Al, Cu, P, and Cr, their inorganic and organic derivatives, individually or as mixtures will function as antifoulants for the reduction of coke during hydrocarbon pyrolysis.

Phosphoric acid and phosphorous acid mono and di-esters or their amine salts, when mixed with the feed to be cracked, for example, ethane, showed a significant increase in run lengths compared to an operation performed without the additives (U.S. Pat. No. 4,105,540).

Pretreating furnace tubes at high temperature with aromatic compounds such as substituted benzenes, naphthalenes and phenanthrenes, prior to introduction of the cracking feed has been shown to reduce catalytic coke formation (U.S. Pat. No. 5,733,438). Cracking a heavy hydrocarbon, preferably a higher olefin stream prior to bringing on the lower hydrocarbons, has been shown to reduce coking (U.S. Pat. No. 4,599, 480). In both cases, a thin layer of catalytically inactive coke formed on the tube surface is claimed to inhibit the propagation of coke formation.

Several patents disclose the use of various Si compounds to lay down a ceramic layer on metal tubes and thus reduce the coke formed in pyrolysis. Compounds such as siloxanes, silanes and silazanes have been used to deposit a silica layer on the metal alloy tubes (U.S. Pats. Nos. 5,424,095; 5,413, 813; and 5,208,069). Silicates have been independently claimed to do the same in patent GB 1552284. In almost all of the examples the coke minimization is of catalytic coke, formed mainly during the early stages of pyrolysis. A patent (U.S. Pat. No. 5,922,192), teaches the use of a silicon compound and a sulfur compound as a mixture that contains Si/S ratio of 1/1 to 5/1 to mitigate coke formation.

Another approach to reduce coking is to passivate the active metal surface of pyrolysis tubes by forming a surface alloy, comprising metals/oxides of metals that are known to not catalyze coke formation. High Temperature Alloys (HTA) are a group of austenitic stainless steels used in industrial processes operating at elevated temperatures above 650° C. These typically contain 118-38% Cr, 18-48% Ni, with the balance being Fe and alloying additives. Iron and nickel are known catalysts for the formation of filamentous carbon during ethylene production and hydrocarbon pyrolysis in general. An oxide layer of chromium or aluminum on the other hand are known to be inhibitors of catalytic coke formation and thus are used to protect these alloys. Protection using these oxides have to be carefully engineered so that physical characteristics and properties of the HTA, such as creep resistance, are not compromised and the oxide layer is stable to harsh conditions typically encountered in hydrocarbon pyrolysis. CoatAlloy™ is a surface coating technology for the inside of HTA tubes for use in an ethylene furnace. Cr—Ti—Si and Al—Ti—Si formulated products are coated on a base alloy surface and heat treated to form either a diffusion protective layer only or a diffusion layer and a enrichment pool layer next to it. In both cases, oxidizing gases are passed to activate the layers by formation of alumina and/or chromia along with titania and silica. The treated tubes have been claimed to significantly reduce catalytic coke formation, minimize carburization of the base alloy tubes, exhibit improved erosion resistance and thermal shock resistance (U.S. Pat. No. 6,093,260). The ethane gas stream used to test the effectiveness of the coating contained 25-30 PPM of sulfur. A combination of sulfur containing compounds such as an alkyl mercaptan- or alkyl disulfide and a nitrogen containing compound such as hydroxylamine, hydrazine or amine oxide are disclosed as useful in pretreating or minimizing coke formation in thermal furnaces (U.S. Pat. No. 6,673,232).

Reduction of coking rates on both quartz and Incoloy surfaces by the use of low concentrations of hexachloroplatinic acid ($H_2PtCl_6$) in the steam used for ethane cracking, have been reported (Industrial & Engineering Chemistry Research, Vol: 37, 3, 901, 1998). Coke formation rates were reduced although the apparent activation energies increased. The reduced effectiveness of the additive at higher temperatures suggests that the primary impact of the additive was on the surface coke formation process.

The typical previous approaches have involved either metal passivation techniques with various additives like sulfur, silicon, phosphorous, etc., or the use of special alloys which reduce coking. These are surface treatments. The use of phosphorus containing compounds has become problematic due to adverse affects on downstream operations. Similarly, the use of amines and derivatives thereof has become problematic due to the formation of NOx and its impact on downstream operations.

The objective of the present invention was to develop improved technology for reducing the formation of coke in commercial thermal cracking furnaces. Reduced coke levels will translate into higher ethylene yields, longer radiant furnace tube life and reduced downtime for decoking of the unit which allows increased total production.

SUMMARY OF THE INVENTION

The invention is a combination useful for reducing or preventing coke formation in thermal cracking furnaces such as ethylene steam crackers. The compounds in the combination of the present invention decompose into compounds such as $H_2S$ which are easily removed in downstream operations. The present invention is directed to a combination including hydrocarbons containing no heteroatoms and hydrocarbons containing sulfur as a heteroatom. The combinations of the present invention comprise
(A) one Or more compounds of the formula:

$$R—S_x—R'$$

wherein R and R' are independently H, alkyl with 1 to 24 carbons straight chain or branched, aryl and x=1 to 5; and
(B) one or more compounds selected from the following group:

wherein $R_1$ and $R_2$ are independently H, alkyl with 1 to 24 carbons straight chain or branched, aryl (e.g., alkylaryl trithiocarbonates);

wherein $R_1$, $R_2$, $R_3$ and $R_4$ are independently H, alkyl with 1 to 24 carbons straight chain or branched, aryl (e.g., alkyl/aryl ethylenes);

RSH wherein R is alkyl of 1 to 24 carbons straight chain or branched (e.g. alkyl/aryl mercaptans);

wherein $R_1$ and $R_2$ are independently H, alkyl with 1 to 24 carbons straight chain or branched, aryl and x=2 to 5 (e.g. alkyl/aryl polysulfides);

wherein $R_1$ and $R_2$ are independently aryl or alkyl substituted aryl with the alkyl group being h or alkyl with 1 to 24 carbons (e.g. diphenylmethane);

wherein $R_1$, $R_2$, $R_3$ and $R_4$ are independently h, alkyl with 1 to 24 carbons straight or branched, aryl (e.g. thiophene or substituted thiopenes); and

Wherein $R_1$, $R_2$, $R_3$, $R_4$, $R_5$, and $R_6$ are independently h, alkyl with 1 to 24 carbons straight or branched, aryl (e.g. substituted disiloxanes).

The invention is also directed towards an improved process for producing olefinic materials like ethylene or propylene by the introduction of the above mixture to the hydrocarbon feed stream to be cracked or to another feed stream such as water/steam prior to either of the streams entering the thermal cracking furnace.

DETAILED DESCRIPTION OF THE INVENTION

There are two basic mechanisms for the formation of coke in ethylene furnaces, catalytic, and non-catalytic. In catalytic coke formation, hydrocarbon is adsorbed on a metal site. As the metal catalyzes the decomposition of the hydrocarbon to elemental carbon, the carbon diffuses through the metal particle. Precipitation of the carbon vapor occurs beneath the surface and the metal particle is actually lifted off from the surface. This process of carbon diffusion and precipitation occurs over and over with the result that filaments (each tipped with a metal particle) of carbon are formed on the inside surface of the cracking tubes. Sulfur and phosphorous derivatives have been used to reduce the amount of catalytic coke formation presumably by passivating the metal surface to reduce or eliminate the phenomena that results in the formation of the carbon filaments.

In non-catalytic coke formation, hydrocarbons decompose in the gas phase thermally via free-radical reactions. Many of these reactions result in the formation of useful compounds like ethylene, propylene, etc. However, various recombination reactions can result in the formation of longer-chain species that can be trapped in the surface carbon filaments. As time goes on, these coke precursors grow and become full-fledged coke. Other long-chain species can exit the reactor and condense in the cooling section. The end result of these non-catalytic reactions is the formation of additional coke and/or heavy condensates, both of which act to reduce ethylene formation.

The majority of the prior art has only addressed preventing the formation of catalytic coke by passivation of the metal surface. The present invention addresses both the formation of catalytic and non-catalytic coke. This approach will lead to lower levels of total coke formation than those previously described and will result in decreased downtime for the commercial units.

In the broadest sense, the present invention combines surface treatment to passivate the metal to reduce catalytic coke formation with the reduction of gas-phase coke formation. Thus, any compound known to passivate metal surfaces in conjunction with compounds known to scavenge free radicals like phenol derivatives, mercaptans, hydrazines, phosphines, etc., are within the scope of the present invention.

The present invention is also an improved process for producing olefinic materials like ethylene or propylene by the introduction of the above components to the hydrocarbon feed stream to be cracked or to another feed stream such as water/steam prior to either of the streams entering the thermal cracking furnace.

The sulfur-containing compounds useful in the present invention have the formula $$R—S_x—R'$$

wherein R and R' are independently H, alkyl with 1 to 24 carbons straight chain or branched, aryl and x=1 to 5

Examples of such compounds include H₂S, methyl-, ethyl-, propyl-, butyl- and higher mercaptans, aryl mercaptans, dimethyl sulfide, diethyl sulfide, unsymmetrical sulfides such as methylethyl sulfide, dimethyl disulfide, diethyl disulfide, methylethyl disulfide, higher disulfides, mixtures of disulfides like merox, sulfur compounds naturally occurring in hydrocarbon streams such as thiophene, alkylthiophenes, benzothiophene, dibenzothiophene, polysulfides such as t-nonyl polysulfide, t-butyl polysulfide, phenols and phosphines. Preferred are alkyl disulfides such as dimethyldisulfide and most preferred is dimethyl sulfide. Preferred treatment ranges of material are from 10 ppm to 1000 ppm relative to the hydrocarbon feed stream. More preferred is 50 to 500 ppm, and most preferred is 100 to 400 ppm. Ratios of the sulfur-containing material to the tree-radical-scavenging component range from 1-0.1 to 1-100 (weight-to-weight).

Component B compounds are selected from the group having the following formulas:

$$R_1R_2CS_3$$

wherein $R_1$ and $R_2$ are independently H, alkyl with 1 to 24 carbons straight chain or branched, aryl (e.g., alkyl/aryl trithiocarbonates);

$$R_1R_2C\!\!=\!\!CR_3R_4$$

wherein $R_1$, $R_2$, $R_3$ and $R_4$ are independently H, alkyl with 1 to 24 carbons straight chain or branched, aryl (e.g., alkyl/ethylenes);

$$RSH$$

wherein R is alkyl of 1 to 24 carbons straight chain or branched (e.g. alkyl/aryl mercaptans);

$$R_1S_xR_2$$

wherein $R_1$ and $R_2$ are independently H, alkyl with 1 to 24 carbons straight chain or branched, aryl and x=2 to 5 (e.g. alkyl/aryl polysulfide);

$$R_1R_2CH_2$$

wherein $R_1$ and $R_2$ are independently aryl or alkyl substituted aryl with the alkyl group being h or alkyl with 1 to 24 carbons (e.g. diphenylmethane);

$$R_1R_2R_3R_4(C_4S)$$

wherein $R_1$, $R_2$, $R_3$ and $R_4$ are independently h, alkyl with 1 to 24 carbons straight or branched, aryl (e.g. thiophene or substituted thiopenes; and $$R_1R_2R_3R_4R_5R_6Si_2O$$

Wherein $R_1$, $R_2$, $R_3$, $R_4$, $R_5$, and $R_6$ are independently h, alkyl with 1 to 24 carbons straight or branched, aryl (e.g. substituted disiloxanes).

Examples of such compounds include 2,4-diphenyl-4-methyl-1-pentene (an alpha-methyl-styrene dimer), triphenylmethane, terpinolene, decalin and thiophene. Preferred ranges of material are from 10 ppm to 1000 ppm relative to the hydrocarbon feed stream. More preferred is 50 to 500 ppm, and most preferred is 100 to 400 ppm. Ratios of the material to the sulfur-containing component range from 1-0.1 to 1-100 (weight-to-weight).

This combination is useful for reducing or preventing coke formation in thermal cracking furnaces such as ethylene steam crackers.

Also, the use of the combinations described above with various surface treatments, pretreatments, special alloys, and special tube coatings described in the prior art is within the scope of this invention.

The present invention discloses a synergy between sulfur chemicals like DMS or DMDS (which passivate the metal surface) and free-radical scavengers, such as an alpha-methyl-styrene dimmer and terpinolene or thiophene which inhibit coke formation in the gas phase by scavenging newly forming coke precursors. Independent of the mechanism, the synergy exhibited between the abovementioned compounds which results in lower levels of total coke formation than either of the components used alone is surprising and unexpected.

A preferred method to practice this invention is to co-inject either separately or together a mixture of DMS or DMDS, and a free-radical scavenger, such as an alpha-methyl-styrene dimmer and terpinolene or thiophene into the hydrocarbon feed stream just prior to its introduction to the furnace. Optimal treatment levels will depend on the operational variables of individual commercial furnaces, but levels between 10 ppm and 1000 ppm of each component should cover the majority of commercial situations.

An advantage of the present invention is that the treatment levels of each component can be tailored and optimized for each commercial unit depending on its operational variables.

In theory, it is desirable that minimal decomposition of the disclosed materials occurs prior to its introduction to the cracking tubes of the furnace. Thus, the method of injection into the furnace is likely to have a major impact oil this. Systems which allow rapid injection with little preheating should give better results.

This invention could also have utility in conjunction with the development of new alloys or tube coatings being developed to reduce or eliminate the formation of catalytic coke.

Many hydrocarbon feed streams contain naturally occurring sulfur compounds like thiophenes, benzothiophenes, dibenzothiophenes, sulfides, and disulfides. The use of the naturally occurring sulfur compounds with the abovementioned free-radical scavengers is within the scope of this invention.

The following Example is offered to illustrate this invention and the modes of carrying out this invention.

EXAMPLES

Example 1

A coupon of HP-40 was made via wire erosion and cleaned with acetone in an ultrasonic bath. The cleaned coupon was hung in a thermo balance and exposed, at 800° C., to the cracking products of the pyrolysis of the feedstock (n-heptane) with and without additives being tested for one hour. The coupon was initially prepared by repeated cycles of coking/decoking. The coupons were pretreated with DMDS, argon, nitrogen and water for 30 minutes to one hour to pre-sulfide the coupon surface. Thereafter, the liquid feedstocks were dosed into the apparatus by means of a micro pump. The feedstock stream was vaporized prior to entering the apparatus. The dilution gases, argon and nitrogen, were introduced as was air during decoking cycles. The cracked products formed during the reaction were cooled to room temperature. Thereafter, a cracked gas sample was analyzed via gas chromatograph and the n-heptane conversion, composition of the cracked products and the cracking severity were determined. Hydrogen and carbon monoxide content in the product gas stream were determine in a second gas chromatograph. The amount of coke formed and the rate of formation were measured and plotted verses time. The coupon was decoked between each experiment. The test conditions are summarized in Table 1 and the results are summarized in Table 2.

TABLE 1

| Feedstock | n-heptane |
|---|---|
| Furnace Temp. (° C.) | 800 |
| Run Tim (min) | 60 |
| Feedstock (g/hr) | 55 |
| Diluent water (ml/h) | 13 |
| Diluent argon (l/hr) | 7 |
| Dilution Ration (g/) | 0.45 |
| DMDS (ppmw) | 200 |
| Additives (ppmw) | 200 |
| Cracking severity (m C$_2$H$_4$/m C$_3$H$_6$) | 21.-2.2 |
| Residence time t (sec) | About 0.6 |

TABLE 2

| Additive | Coke (mg) | % | Coke Rate | % |
|---|---|---|---|---|
| N-heptane +200 ppm DMDS | 36.30 | | 407 | |
| N-heptane +200 ppm DMDS + 200 ppm additive | 44.72 | 87 | 544 | 85 |
| N-heptane +200 ppm DMDS | 66.50 | | 869 | |
| N-heptane +200 ppm DMDS + 200 ppm additive | 61.75 | 84 | 811 | 87 |
| N-heptane +200 ppm DMDS | 80.52 | | 994 | |
| N-heptane +200 ppm DMDS | 58.75 | | 624 | |
| N-heptane +200 ppm DMDS + 300 ppm additive | 70.03 | 79 | 714 | 82 |
| N-heptane +200 ppm DMDS | 117.62 | | 1124 | |
| N-heptane +200 ppm DMDS + 300 ppm additive | 99.83 | 80 | 999 | 82 |
| N-heptane +200 ppm DMDS | 131.35 | | 1293 | |

The data in Table 2 shows that the use of the additives at a level of 200 ppm resulted in approximately a 15% reduction in coke formation and when the additives treatment levels were increased to 300 ppm, the coke formation levels decreased by about 20%.

While the present invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed:

1. A combination useful for reducing or preventing coke formation in thermal cracking furnaces, the combination being comprised of (A) at least one of dimethyldisulfide and dimethyl sulfide; and (B) a free radical scavenger selected from alpha-methyl-styrene dimmer and terpinolene wherein both component A and B are present at a concentration relative to the hydrocarbon feed stream of 100-300 ppm and at a ratio to each other ranging from 1-0.1 to 1-100 (weight-to-weight).

* * * * *